(12) United States Patent
Yamashita et al.

(10) Patent No.: US 8,048,681 B2
(45) Date of Patent: Nov. 1, 2011

(54) METHODS FOR NUCLEIC ACID ISOLATION AND INSTRUMENTS FOR NUCLEIC ACID ISOLATION

(75) Inventors: Yoshihiro Yamashita, Hitachinaka (JP); Toshinari Sakurai, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 395 days.

(21) Appl. No.: 11/529,418

(22) Filed: Sep. 29, 2006

(65) Prior Publication Data

US 2007/0106071 A1    May 10, 2007

(30) Foreign Application Priority Data

Nov. 4, 2005   (JP) .................. 2005-320733

(51) Int. Cl.
*C07H 21/00*   (2006.01)
(52) U.S. Cl. ........... 436/111; 436/17; 536/25.4; 422/69; 435/6; 435/287.2; 435/287.7; 210/294
(58) Field of Classification Search .................. None
See application file for complete search history.

(56) References Cited

U.S. PATENT DOCUMENTS

| | | | |
|---|---|---|---|
| 6,277,648 B1 * | 8/2001 | Colpan | 436/177 |
| 2002/0007054 A1 | 1/2002 | Sakurai et al. | |
| 2004/0247490 A1 * | 12/2004 | Olivier et al. | 422/101 |
| 2005/0084886 A1 * | 4/2005 | Igarashi et al. | 435/6 |
| 2005/0186607 A1 * | 8/2005 | Shoji et al. | 435/6 |
| 2006/0270843 A1 * | 11/2006 | Hall et al. | 536/25.4 |

FOREIGN PATENT DOCUMENTS

| | | |
|---|---|---|
| EP | 0 819 696 A2 | 3/1990 |
| EP | 1 571 437 A1 | 9/2005 |
| JP | 2000-505295 | 5/2000 |
| JP | 2002-187897 | 7/2002 |
| JP | 2002-534080 | 10/2002 |
| JP | 2004-201607 | 7/2004 |
| JP | 3619514 | 11/2004 |
| JP | 2004-340839 | 12/2004 |
| JP | 2005-137295 | 6/2005 |

(Continued)

OTHER PUBLICATIONS

Tadashi Yoshida, et al., Myocardin is a key regulator of CArG-dependent transcription of multiple smooth muscle marker genes, 2003, Circulation Research (pub: American Heart Association), 92(8), pp. 856-864.*

(Continued)

*Primary Examiner* — In Suk Bullock
*Assistant Examiner* — Timothy G Kingan
(74) *Attorney, Agent, or Firm* — McDermott Will & Emery LLP

(57) ABSTRACT

The present invention relates to a technique for efficient isolation of long nucleic acids and short nucleic acids from a sample containing long nucleic acids and short nucleic acids via safe and convenient operations. Specifically, long nucleic acids and short nucleic acids are isolated from a sample containing nucleic acids by mixing a chaotropic agent with the sample containing nucleic acids, allowing the mixed solution to pass at least twice through a first solid phase containing silica that has passage pores having predetermined pore sizes, allowing the mixed solution to pass at least twice through a second solid phase containing silica that has passage pores having pore sizes smaller than those of the first solid phase containing silica, and separately recovering nucleic acids that have bound to the first solid phase containing silica and those that have bound to the second solid phases containing silica.

9 Claims, 3 Drawing Sheets

FOREIGN PATENT DOCUMENTS

| | | |
|---|---|---|
| JP | 2005-241299 | 9/2005 |
| WO | WO 97/30062 | 8/1997 |
| WO | WO 00/40697 A1 | 7/2000 |
| WO | WO 02/078846 | 10/2002 |

OTHER PUBLICATIONS

Piotr Chomczynski et al. "Single-Step Method of RNA Isolation by Acid Guanidinium Thiocyanate-Phenol-Chloroform Extraction" Analytical Biochemistry 162, 156-159 (1987).

Bert Vogelstein et al. "Preparative and Analytical Purification of DNA from Agarose" Proc. Natl. Acad. Sci. USA vol. 76, No. 2 pp. 615-619, 1979.

R Boom et ali. "Rapid and Simple Method of Purification of Nucleic Acids" Department of Virology, Academic Medical Center, Meibergdereef 15, 1105 AZ Amsterdam, received Aug. 2, 1989.

German Office Action issued in German Patent Application No. 10 2006 045 391.3, dated Mar. 20, 2007.

* cited by examiner

METHODS FOR NUCLEIC ACID ISOLATION AND INSTRUMENTS FOR NUCLEIC ACID ISOLATION

CLAIM OF PRIORITY

The present application claims priority from Japanese application JP 2005-320733 filed on Nov. 4, 2005, the content of which is hereby incorporated by reference into this application.

BACKGROUND OF THE INVENTION

1. Field of the Invention

The present invention relates to a technique for efficient isolation of long nucleic acids and short nucleic acids from a sample containing long nucleic acids and short nucleic acids via safe and convenient operations. In addition, the present invention can be utilized as a technique for isolation of genomic DNA and total RNA (e.g., messenger RNA, ribosomal RNA, and transfer RNA) or of genomic DNA and plasmid DNA.

2. Background Art

Nucleic acids are related to genetic information in organisms, and exist in various forms such as genomic DNA, plasmid DNA, messenger RNA, ribosomal RNA, and transfer RNA, which are functionally different from one another.

Based on analysis of these nucleic acids, very important molecular biological information can be obtained. Upon analysis of various types of nucleic acids, in general, it is preferable to carry out pretreatment comprising isolation of nucleic acids of interest from a biological sample containing different types of nucleic acids. For instance, upon messenger RNA analysis for the purpose of gene expression analysis, total RNA is isolated from genomic DNA, which can act as an inhibitor during messenger RNA analysis.

In general, phenol/chloroform extraction has been known as a method for total RNA isolation from genomic DNA in a biological sample (Analytical Biochemistry, 162, 156-159 (1989)). This method comprises: (1) dissolving a biological sample in a guanidine thiocyanate solution and adding an acidic buffer solution, a phenol solution, and a chloroform solution thereto in that order, followed by mixing; (2) separating the mixture into an aqueous phase containing RNA, and an interphase and an organic solvent phase containing insolubilized DNA and denatured proteins via centrifugation; (3) adding ethanol or isopropanol to the aqueous phase containing RNA; and (4) allowing insolubilized RNA to selectively precipitate via centrifugation. Compared with conventional ultracentrifugation methods, this method is more efficient in terms of RNA isolation; however, highly hazardous phenol and chloroform must be used in the method, which is problematic.

As examples of a method for nucleic acid isolation that requires no use of phenol, chloroform, or the like, and requires no operations such as ethanol precipitation or isopropanol precipitation, methods utilizing nucleic acid binding properties with reference to a solid phase containing silica in the presence of a chaotropic agent have been known (B. Vogelstein and D. Gillespie, Proc. Natl. Acad. Sci. USA, 76 (2), 615-619 (1979), R. Boom et al., J. Clin. Microbiol. 28 (3), 495-503 (1990)). Also, methods for DNA and RNA isolation to which the latter method is applied have been reported (JP Patent Publication (Kokai) No. 2004-340839 A, No. 2002-187897 A, No. 2000-505295 A, No. 2002-534080 A, and No. 2004-201607 A). However, such methods result in insufficient DNA and RNA isolation, so that isolated RNA contains a predetermined amount of DNA.

SUMMARY OF THE INVENTION

It is an objective of the present invention to efficiently isolate long nucleic acids and short nucleic acids from a sample containing long nucleic acids and short nucleic acids via safe and convenient operations.

As a result of intensive studies in order to attain the above objective, the present inventors have found that a mixed solution of a chaotropic agent and a sample containing long nucleic acids and short nucleic acids is allowed to pass at least twice through a solid phase containing silica that has liquid passage pores having pore sizes that result in high contact efficiency with long nucleic acids and low contact efficiency with short nucleic acids such that long nucleic acids are selectively and efficiently allowed to bind to the solid phase containing silica so as to be isolated from short nucleic acids.

Specifically, the present invention relates to a method for nucleic acid isolation comprising the steps of:

mixing a chaotropic agent with a sample containing long nucleic acids and short nucleic acids;

allowing the mixed solution to pass at least twice through a first solid phase containing silica that has passage pores having predetermined pore sizes;

allowing the mixed solution to pass at least twice through a second solid phase containing silica that has passage pores having pore sizes smaller than those of the first solid phase containing silica; and separately recovering nucleic acids that have bound to the first solid phase containing silica and those that have bound to the second solid phase containing silica.

In the aforementioned method, preferably, the mixed solution is allowed to pass at least twice through the first and second solid phases containing silica in both directions to such solid phases containing silica (e.g., both upward and downward directions).

In accordance with the method of the present invention, nucleic acids that bind to the first solid phase containing silica are long nucleic acids composed of not less than 20000 and preferably not less than 50000 deoxyribonucleotides or ribonucleotides, and nucleic acids that bind to the second solid phase containing silica are short nucleic acids composed of not more than 10000 and preferably not more than 5000 deoxyribonucleotides or ribonucleotides.

In such case, preferably, passage pores of the first solid phase containing silica have pore sizes of 20 to 25 μm. At the same time, preferably, passage pores of the second solid phase containing silica have pore sizes of 0.1 to 10 μm.

In one embodiment, nucleic acids that bind to the first solid phase containing silica are genomic DNA and nucleic acids that bind to the second solid phase containing silica are RNA. Alternatively, nucleic acids that bind to the first solid phase containing silica are genomic DNA and nucleic acids that bind to the second solid phase containing silica are plasmid DNA. Thus, total RNA, plasmid DNA, or genomic DNA can be selectively and efficiently isolated from a biological sample.

Further, in accordance with the present invention, an instrument for nucleic acid isolation used in the method for nucleic acid isolation of the present invention is provided. The instrument for nucleic acid isolation is equipped with a solid phase containing silica and a passage opening through which the mixed solution of a sample containing nucleic acids and a chaotropic agent is aspirated and discharged. The mixed solution is aspirated or discharged from the passage opening by pressure control. Thus, the mixed solution is transferred between spaces separated by the solid phase containing silica such that the mixed solution is allowed to pass at least twice through the solid phase containing silica.

Further, in accordance with the present invention, a kit for nucleic acid isolation is provided, which comprises an instrument for nucleic acid isolation of the present invention and at least one member selected from the group consisting of a chaotropic agent, an organic solvent, a washing reagent, and an elution reagent.

Examples of a chaotropic agent that can be used include guanidine thiocyanate, sodium thiocyanate, guanidine hydrochloride, sodium iodide, and potassium iodide. Examples of an organic solvent that can be used include ethanol and diethylene glycol dimethyl ether.

In accordance with the present invention, long nucleic acids and short nucleic acids can be efficiently isolated from a sample containing long nucleic acids and short nucleic acids via safe and convenient operations. Thus, for instance, genomic DNA and total RNA (messenger RNA, ribosomal RNA, or transfer RNA) or genomic DNA and plasmid DNA can be efficiently isolated.

DESCRIPTION OF THE PREFERRED EMBODIMENTS

Figure 1:
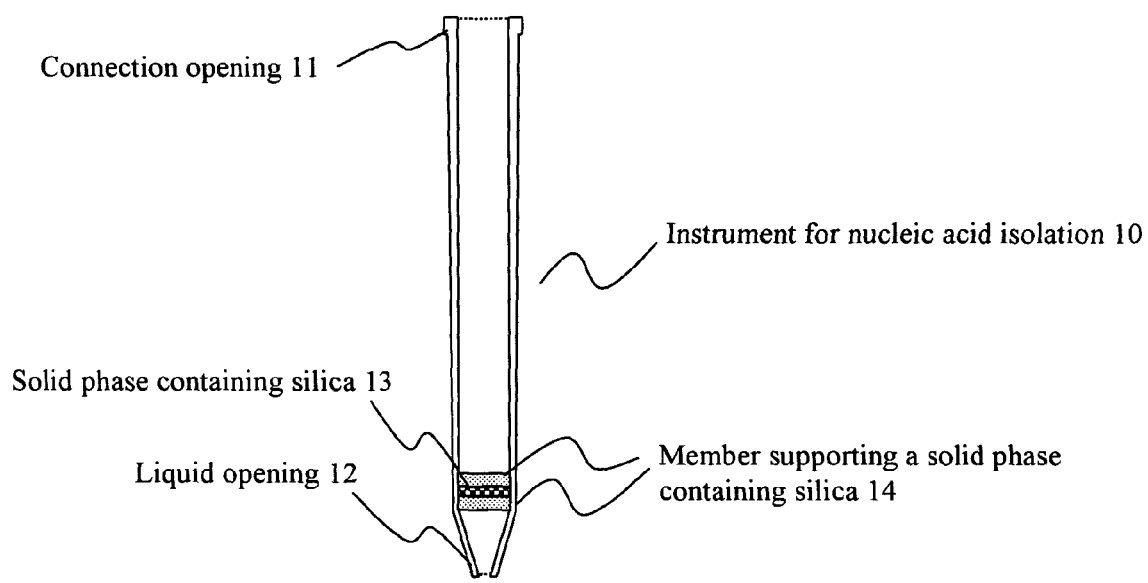
FIG. 1 schematically shows an instrument for nucleic acid isolation.

Hereafter, the present invention will be described in detail.

The present invention relates to a method for nucleic acid isolation, wherein nucleic acids are efficiently isolated depending on their lengths (long nucleic acids and short nucleic acids). In accordance with the present invention, a sample containing nucleic acids to be isolated is mixed with a chaotropic agent. Then, the mixed solution is allowed to pass at least twice through a first solid phase containing silica that has passage pores having pore sizes that result in high contact efficiency with long nucleic acids and low contact efficiency with short nucleic acids such that long nucleic acids are selectively and efficiently allowed to bind to the first solid phase containing silica. Thereafter, the mixed solution that has passed through the first solid phase containing silica is allowed to pass at least twice through a second solid phase containing silica that has passage pores having pore sizes that result in high contact efficiency with short nucleic acids such that short nucleic acids are allowed to bind to the second solid phase containing silica. Thus, nucleic acids that have bound to the first and second solid phases containing silica are separately recovered using elution reagents such that long nucleic acids and short nucleic acids can be efficiently isolated.

Samples (particularly biological samples) containing nucleic acids that are applied to the present invention contain two or more types of nucleic acids having different lengths (long nucleic acids and short nucleic acids). Examples thereof include blood, biological tissue, cultured cells, and bacteria. In addition, the term "nucleic acid" indicates a chain polymer composed of deoxyribonucleotides or ribonucleotides that bind to one another via phosphodiester bonds and a complex comprising such polymers that bind to one another via hydrogen bonds or the like. Further, such nucleic acids may be single- or double-stranded.

In accordance with the present invention, long nucleic acids that are allowed to bind to the first solid phase containing silica are composed of preferably not less than 20000 and more preferably not less than 50000 deoxyribonucleotides or ribonucleotides. For instance, genomic DNA, genomic RNA, plasmid DNA, and nucleic acids that are fragments thereof can be applied to the present invention. Specifically, examples of long nucleic acids that can be applied to the present invention include genomic DNA having lengths of preferably not less than 10 kb and more preferably not less than 25 kb and genomic RNA having lengths of preferably not less than 20 kb and more preferably not less than 50 kb.

Further, short nucleic acids that are allowed to bind to the second solid phase containing silica are composed of preferably not more than 10000 and more preferably not more than 5000 deoxyribonucleotides or ribonucleotides. For instance, messenger RNA, ribosomal RNA, transfer RNA, cDNA, plasmid DNA, and amplified DNA obtained via PCR can be applied to the present invention. Specifically, examples of short nucleic acids that can be applied to the present invention include double strand cDNA having lengths of preferably not more than 5 kb and more preferably not more than 2.5 kb and messenger RNA having lengths of preferably not more than 10 kb and more preferably not more than 5 kb.

Examples of chaotropic agents to be added to a sample containing nucleic acids include guanidine thiocyanate, sodium thiocyanate, guanidine hydrochloride, sodium iodide, and potassium iodide. The concentration of the chaotropic agent added is preferably 1.0 to 4.0 mol/l in the mixed solution to which an organic solvent has been added (see R. Boom et al., J. Clin. Microbiol. 28 (3), 495-503 (1990)).

When a biological sample is used, in addition to a chaotropic agent, a surfactant, a protein denaturant, protease, or the like may be added thereto. Further, it is preferable that the mixed solution be subjected to physical treatment using a stirrer, a homogenizer, or the like, resulting in promotion of dissolution of a biological sample and release of nucleic acids.

To the mixed solution containing a sample containing nucleic acids and a chaotropic agent, it is preferable to add an organic solvent so as to promote the binding of nucleic acids to a solid phase containing silica.

Examples of an organic solvent that can be used include a combination of one or more compounds selected from the group consisting of aliphatic alcohols, aliphatic ethers, aliphatic esters, and aliphatic ketones.

Examples of aliphatic alcohols that can be used include methanol, ethanol, 2-propanol, 2-butanol, and polyethylene glycol. Examples of aliphatic ethers that can be used include diethylene glycol dimethyl ether, diethylene glycol diethyl ether, ethylene glycol dimethyl ether, ethylene glycol diethyl ether, propylene glycol dimethyl ether, propylene glycol diethyl ether, and tetrahydrofuran. Examples of aliphatic esters that can be used include ethyl lactate and propylene glycol monomethyl ether acetate. Examples of aliphatic ketones that can be used include acetone, hydroxyacetone, and methylketone. Particularly, ethanol, diethylene glycol dimethyl ether, and the like are preferable.

The solid phase containing silica used in the present invention comprises a silica compound containing silicon dioxide. Examples of such silica compound include glass particles (fine particles), silica particles (fine particles), glass fiber, silica fiber, diatomaceous earth, and disrupted products thereof. The solid phase containing silica has a plurality of passage pores therein such that a solution can pass therethrough. As long as the solid phase containing silica is formed as described above, it may be in the form of a disk, fiber, or aggregate of particles, but it is not particularly limited thereto.

Preferably, the first solid phase containing silica has passage pores having pore sizes of 20 to 25 µm, resulting in high contact efficiency with long nucleic acids and low contact efficiency with short nucleic acids. This is because, when pore sizes are below such range, the contact efficiency of the solid phase containing silica with short nucleic acids increases so that short nucleic acids bind thereto, while on the other hand, when pore sizes are above such range, the contact efficiency of the solid phase containing silica with long nucleic acids decreases so that the amount of long nucleic acids binding thereto decreases.

The mixed solution is required to pass at least twice thorough the first solid phase containing silica. This is because a single passage of the mixed solution results in low binding efficiency of the solid phase containing silica with long nucleic acids so that a sufficient amount of long nucleic acids cannot be recovered. In addition, with an increase of numbers of liquid passage through the first solid phase containing silica, the amount of long nucleic acids binding thereto increases; however, the amount of short nucleic acids binding thereto does not substantially increase. Thus, when the mixed solution is allowed to pass at least twice through the first solid phase containing silica, it becomes possible to selectively increase the amount of long nucleic acids binding thereto so as to improve the long nucleic acid recovery rate.

Meanwhile, preferably, the second solid phase containing silica has passage pores having pore sizes of 0.1 to 10 µm, resulting in high contact efficiency with short nucleic acids. In order to improve binding efficiency of the solid phase containing silica with short nucleic acids, it is preferable to increase numbers of passage of the mixed solution through the solid phase containing silica and to decrease passage pore sizes within a range that is suitable for the sizes of the nucleic acids.

The aforementioned first and second solid phases containing silica are immobilized on a single or on different hollow member(s) such as tip(s), syringe(s), and column(s). Such a member is equipped with a passage opening through which the mixed solution is aspirated and discharged, a connection opening at which a pressure control instrument or the like is connected for pressure control of the hollow space, and a solid phase containing silica in the hollow space thereof. The member is designed in a manner such that: the hollow space is depressurized or pressurized using a pressure control instrument that is connected at the connection opening; the mixed solution is aspirated or discharged via the passage opening; and the mixed solution is transferred between spaces separated by the solid phase containing silica so as to pass at least twice through the solid phase containing silica.

For instance, in the case of a tip on which a solid phase containing silica has been immobilized, the inside of the tip is depressurized using a syringe or pipetter that has been connected to the connection opening, the mixed solution is aspirated so as to pass through the solid phase containing silica, the inside of the tip is pressurized, and the mixed solution is discharged so as to pass through the solid phase containing silica. These steps are repeated such that the mixed solution is allowed to pass at least twice through the solid phase containing silica. In addition, before connecting a pressure control instrument, it is possible to introduce a liquid via the connection opening. Thus, after introducing a liquid, it is possible to connect a pressure control instrument to the tip so as to discharge the liquid via the passage opening.

In addition, in the case of a syringe in which the solid phase containing silica has been immobilized, the inside of the syringe is depressurized using a plunger previously provided at a connection opening, the mixed solution is aspirated so as to pass through the solid phase containing silica, the inside of the syringe is pressurized, and the mixed solution is discharged so as to pass through the solid phase containing silica. These steps are repeated such that the mixed solution is allowed to pass at least twice through the solid phase containing silica.

Similar steps can be carried out in the case of a spin column in which the solid phase containing silica has been immobilized. For instance, when using such spin column in accordance with known spin column systems, the mixed solution is introduced into the spin column and the mixed solution is allowed to pass through the solid phase containing silica via centrifugal force. Further, the mixed solution that has passed through the solid phase containing silica is repeatedly introduced into the spin column such that the mixed solution is allowed to pass at least twice through the solid phase containing silica.

Impurities in each solid phase containing silica to which nucleic acids have bound are removed by allowing a washing reagent to pass through the solid phase containing silica. Such washing reagent is required to maintain the binding between nucleic acids and the solid phase containing silica and to remove impurities binding to the solid phase containing silica. For example, an aqueous solution containing 80% (v/v) ethanol and a buffer solution containing 80% (v/v) ethanol with a low salt concentration can be used.

Then, an elution reagent is allowed to pass through each solid phase containing silica after washing such that nucleic acids that have bound to the solid phase containing silica are eluted. Such elution reagent is required to elute nucleic acids to be eluted from the solid phase containing silica. For example, nuclease-free water and a nuclease-free buffer solution with a low salt concentration can be used.

In accordance with the present invention, the aforementioned instruments for nucleic acid isolation and kits for nucleic acid isolation containing the instruments are provided. Such kits contain instruments for nucleic acid isolation, and at least one member of the group consisting of a chaotropic agent, an organic solvent, a washing reagent, and an elution reagent described above. In addition, the aforementioned methods for nucleic acid isolation (usage of instruments for nucleic acid isolation), handling of reagents, and the like are described on the package or in the package insert of the kit according to need.

EXAMPLES

The present invention is hereafter described in detail with reference to the following examples, although the technical scope of the present invention is not limited thereto.

[A] Samples, Reagents, and Instruments

1. Samples 1.1 Long Nucleic Acid

Genomic DNA (an isolated product from human blood using QIAamp DNA Blood Mini Kit*)

* QIAamp DNA Blood Mini Kit (QIAGEN: genomic DNA having lengths not more than 50 kb (mainly 20-30 kb) are isolated via such kit)

1.2 Short Nucleic Acid pBR322 DNA (length: 4361 bp) (MBI Fermentas)

1.3 Biological Sample

Human blood (with the addition of anticoagulant EDTA-2Na)

2. Reagents
2.1 Red Blood Cell Lysis Reagent
  155 mM $NH_4Cl$
  10 mM $KHCO_3$
  0.1 mM EDTA.2Na
2.2 Chaotropic Reagent A
  6M guanidine hydrochloride
  50 mM MES
2.3 Chaotropic Reagent B
  4M guanidine thiocyanate
  25 mM sodium citrate (pH 7.5)
  1% β-mercaptoethanol
2.4 Organic Solvent A
  Ethanol
2.5 Organic Solvent B
  40% (v/v) diethylene glycol dimethyl ether aqueous solution
2.6 Washing Reagent
  80% (v/v) ethanol aqueous solution
2.7 Elution Reagent A
  TE (pH 8.0) (Wako Pure Chemical)
2.8 Elution Reagent B
  $H_2O$ (nuclease-free) (Wako Pure Chemical)
3. Instruments for Long Nucleic Acid Isolation
3.1 Solid Phase Containing Silica
  A glass fiber filter (Standard 14) (pore size: approx 23 μm) (Whatman)
3.2 Member Holding a Solid Phase Containing Silica
  A sintered plate of polypropylene particles (pore size: approx 100 μm) (thickness: 1.5 mm)
3.3 Instrument for RNA Isolation
  FIG. 1 shows a constitutional example of an instrument for long nucleic acid isolation. The instrument for nucleic acid isolation 10 has an appearance like a pipette tip. The instrument is equipped with a passage opening 12 through which a mixed solution is aspirated and discharged and a connection opening 11 to which a pressure control instrument that depressurizes or pressurizes the inside of the tip is connected. In addition, the instrument accommodates a solid phase containing silica 13 inside itself. On each side of the solid phase containing silica, a disc-shaped member holding a solid phase containing silica 14 is connected. These members holding a solid phase containing silica have a number of pores, through which liquid and gas pass. In this instrument, when a tip portion of the passage opening is in contact with liquid, a hollow space is depressurized or pressurized using a pressure control instrument that has been connected at the connection opening such that liquid can be aspirated or discharged via the passage opening so as to pass through the solid phase containing silica. In addition, before connecting such pressure control instrument, it is possible to introduce a liquid via the connection opening. In such case, a pressure control instrument is connected after the introduction of the liquid such that the liquid can be discharged via the passage opening. In the Examples, a solid phase containing silica that had been cut into a disc shape with a diameter of 4.2 mm was used while being sandwiched by two members holding a solid phase containing silica with a diameter of 4.1 mm so as to be press-fitted into a hollow space with an inner diameter of 4 mm.
4. Instrument for Short Nucleic Acid Isolation
4.1 Solid Phase Containing Silica
  A glass fiber filter (GF/D) (pore size: approx 2.7 μm) (Whatman)
4.2 Member Holding a Solid Phase Containing Silica
  A sintered plate of polypropylene particles (pore size: approx 100 μm) (thickness: 1.5 mm)
4.3 Instrument for RNA Isolation
  An instrument for short nucleic acid isolation has a structure similar to that of an instrument for long nucleic acid isolation.
[B] Method for Nucleic Acid Isolation
1. Method for Nucleic Acid Isolation from a Nucleic Acid Solution
  (1) A TE solution (10 μl) containing 1 μg of a nucleic acid sample is prepared.
  (2) A chaotropic reagent A (0.3 ml) is added thereto, followed by mixing.
  (3) An organic solvent A (0.3 ml) is added thereto, followed by mixing.
  (4) A syringe is attached to a connection opening of an instrument for nucleic acid isolation such that the mixed solution is repeatedly aspirated and discharged a given number of times via the passage opening of the instrument for nucleic acid isolation. Note that, in the case of a single liquid passage, the mixed solution is introduced via the connection opening before the attachment of the syringe so that it can be discharged via the passage opening.
  (5) A washing reagent (1 ml) is aspirated and discharged once via the passage opening of the instrument for nucleic acid isolation.
  (6) Step (5) is repeated 3 times such that the washing reagent is completely discharged.
  (7) An elution reagent A (0.05 ml) is repeatedly aspirated and discharged 10 times via the passage opening of the instrument for nucleic acid isolation.
  (8) The elution reagent is recovered as a nucleic acid isolation solution.
2. Method for Nucleic Acid Isolation from Blood
  (1) A red blood cell lysis reagent (3 ml) is added to 0.6 ml of whole blood, followed by mixing.
  (2) The mixture is incubated on ice for 5 minutes.
  (3) Centrifugation is performed at 400×g for 10 minutes.
  (4) The supernatant of the resultant is removed.
  (5) A red blood cell lysis reagent (1.2 ml) is added to the pellet obtained, followed by mixing.
  (6) Centrifugation is performed at 400×g for 10 minutes.
  (7) The supernatant of the resultant is removed such that a white blood cell pellet is obtained.
  (8) A chaotropic reagent B (0.3 ml) is added to a white blood cell pellet, followed by mixing.
  (9) The mixed solution is homogenized using a homogenizer (QIA shredder homogenizer) (QIAGEN).
  (10) An organic solvent B (0.3 ml) is added thereto, followed by mixing.
  (11) A syringe is attached to a connection opening of an instrument for long nucleic acid isolation such that the mixed solution is repeatedly aspirated and discharged 3 times via the passage opening of the instrument for nucleic acid isolation.
  (12) A washing reagent (1 ml) is aspirated and discharged once via the passage opening of the instrument for nucleic acid isolation.
  (13) Step (12) is repeated 3 times such that the washing reagent is completely discharged.
  (14) An elution reagent A (0.2 ml) is repeatedly aspirated and discharged 10 times via the passage opening of the instrument for nucleic acid isolation.
  (15) The elution reagent is recovered as a long nucleic acid isolation solution.
  (16) A syringe is attached to the connection opening of the instrument for short nucleic acid isolation such that the mixed solution that has been discharged in step (11) from the passage opening of the instrument for nucleic acid isolation is repeatedly aspirated and discharged 10 times.

(17) A washing reagent (1 ml) is aspirated and discharged once via the passage opening of the instrument for nucleic acid isolation.

(18) Step (17) is repeated 3 times such that the washing reagent is completely discharged.

(19) An elution reagent B (0.05 ml) is repeatedly aspirated and discharged 10 times via the passage opening of the instrument for nucleic acid isolation.

(20) The elution reagent is recovered as a short nucleic acid isolation solution.

[C] Method for Evaluating Isolated Nucleic Acids

1. Quantification of Nucleic Acid Concentration

A nucleic acid solution was diluted to an adequate amount such that the absorbance at 260 nm was determined using a spectrophotometer (GeneSpec 1, Hitachi Naka Instrument). The absorbance at 260 nm of a DNA solution (50 μg/ml) was determined to be 1 such that the DNA concentration of the nucleic acid solution was calculated.

2. Nucleic Acid Electrophoresis

With the use of a 1.25% agarose gel (Reliant RNA Gel System, FMC), electrophoresis (10 V/cm, 40 minutes) was performed on a nucleic acid solution that had been subjected to formamide denaturation. After electrophoresis, agarose gel was dyed with ethidium bromide and photographed photography under UV irradiation.

[D] Verification Experiment 1

Genomic DNA was used as a long nucleic acid sample and pBR322 DNA was used as a short nucleic acid sample. In accordance with the aforementioned method for nucleic acid isolation from a nucleic acid solution, nucleic acid isolation was carried out using an instrument for long nucleic acid isolation and an instrument for short nucleic acid isolation. In a binding step, each sample was introduced via an opening of an instrument for nucleic acid isolation and discharged via a passage opening in a one-way direction. In addition, each sample was aspirated and discharged via the passage opening 1, 5, or 10 times.

Figure 2:
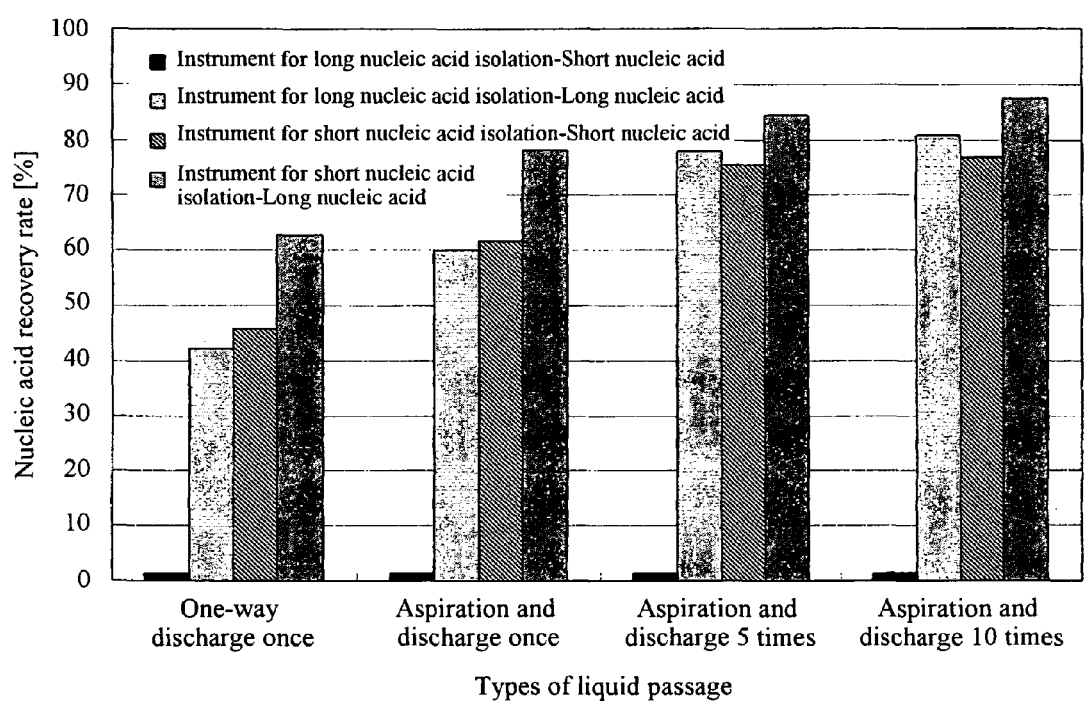
FIG. 2 shows relationships between numbers of passage and nucleic acid recovery rates for combinations of instruments for nucleic acid isolation and nucleic acid samples.

The following table shows nucleic acid recovery rates in each of instruments for nucleic acid isolation, nucleic acid samples, and numbers of liquid passage. In addition, FIG. 2 shows relationships between types of liquid passage and nucleic acid recovery rates in each of instruments for nucleic acid isolation and nucleic acid samples. Further, nucleic acid recovery rate are shown as percentages of amounts of nucleic acids isolated relative to amounts of nucleic acids introduced.

TABLE 1

| Instrument for nucleic acid isolation | Nucleic acid sample | Types of liquid passage | Nucleic acid recovery rate [%] |
|---|---|---|---|
| Instrument for long nucleic acid isolation | Long nucleic acid | One-way | 42 |
| | | Aspiration and discharge once | 60 |
| | | Aspiration and discharge 5 times | 78 |
| | | Aspiration and discharge 10 times | 81 |
| | Short nucleic acid | One-way | 1 |
| | | Aspiration and discharge once | 1 |
| | | Aspiration and discharge 5 times | 1 |
| | | Aspiration and discharge 10 times | 1 |
| Instrument for short nucleic acid isolation | Long nucleic acid | One-way | 63 |
| | | Aspiration and discharge once | 78 |
| | | Aspiration and discharge 5 times | 84 |
| | | Aspiration and discharge 10 times | 87 |
| | Short nucleic acid | One-way | 46 |
| | | Aspiration and discharge once | 62 |
| | | Aspiration and discharge 5 times | 75 |
| | | Aspiration and discharge 10 times | 77 |

In the case of the instrument for long nucleic acid isolation, the long nucleic acid recovery rate increased as the number of liquid passage increased; however, the short nucleic acid recovery rate was extremely low regardless of the number of liquid passage. Meanwhile, in the case of the instrument for short nucleic acid isolation, the long nucleic acid recovery rate and the short nucleic acid recovery rate increased as the number of liquid passage increased.

The results indicate that long nucleic acids are allowed to selectively bind to the instrument for long nucleic acid isolation, while short nucleic acids are not allowed to bind thereto. In addition, it is indicated that, with the use of the instrument for short nucleic acid isolation, short nucleic acids that do not bind to the instrument for long nucleic acid isolation are allowed to bind such that long nucleic acids and short nucleic acids can be efficiently isolated.

[E] Verification Experiment 2

In accordance with the method for nucleic acid isolation from blood, nucleic acid isolation was carried out using human blood as a biological sample, an instrument for long nucleic acid isolation, and an instrument for short nucleic acid isolation.

Figure 3:
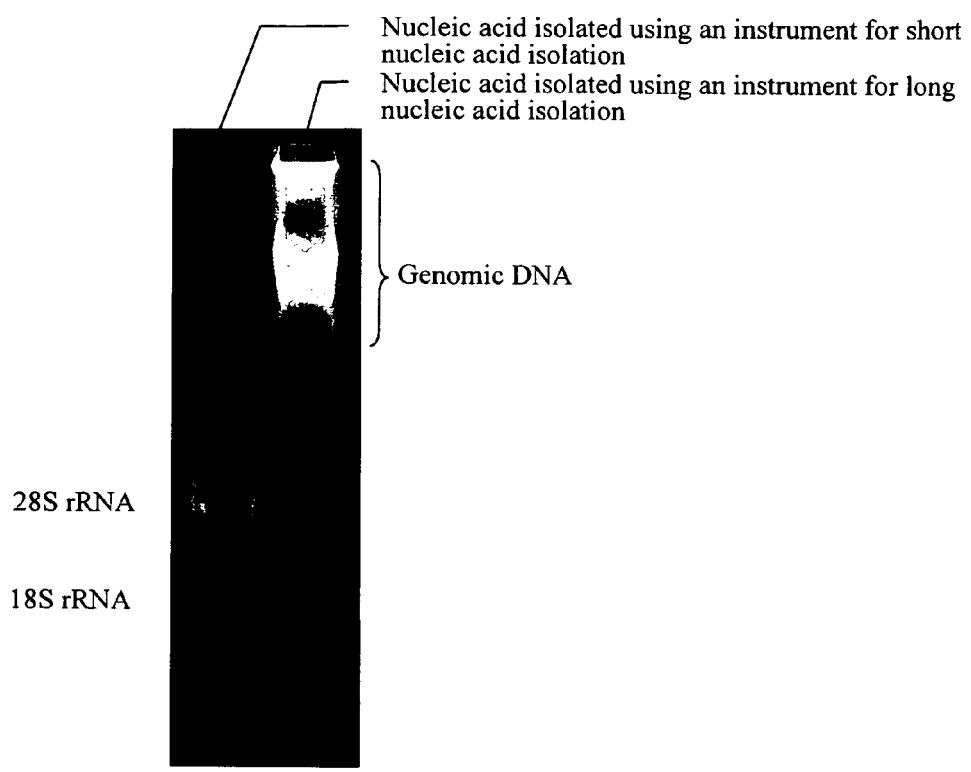
FIG. 3 shows results of electrophoresis of nucleic acids that were isolated using an instrument for long nucleic acid isolation and an instrument for short nucleic acid isolation.

FIG. 3 shows results of electrophoresis of nucleic acids isolated by the instrument for long nucleic acid isolation and nucleic acids isolated by the instrument for short nucleic acid isolation. The nucleic acids isolated by the instrument for long nucleic acid isolation mainly contain genomic DNA; they contain substantially no RNA. Meanwhile, the nucleic acids isolated by the instrument for short nucleic acid isolation mainly contain ribosomal RNA (about 5000 b; 28S rRNA), ribosomal RNA (about 1900 b; 18S rRNA), and messenger RNA; they contain substantially no genomic DNA.

The results indicate that genomic DNA and total RNA can be efficiently isolated from a biological sample containing genomic DNA and total RNA using an instrument for long nucleic acid isolation and an instrument for short nucleic acid isolation.

All publications, patents, and patent applications cited herein are incorporated herein by reference in their entirety.

What is claimed is:

1. A method for nucleic acid isolation, comprising the steps of:
   mixing a chaotropic agent with a sample containing nucleic acids;
   allowing the mixed solution to pass at least twice through a first solid phase containing silica that has passage pores having predetermined pore sizes;
   allowing the mixed solution passed through the first solid phase to pass at least twice through a second solid phase containing silica that has passage pores having pore sizes smaller than those of the first solid phase containing silica;
   wherein passage pores of the first solid phase containing silica have pore sizes of 20 to 25 µm and passage pores of the second solid phase containing silica have pore sizes of 0.1 to 10 µm,
   thereby, separating and capturing nucleic acids according to the base sequence lengths by the action of the first and second solid phases with the different pore sizes; and
   separately recovering nucleic acids that have bound to the first solid phase containing silica and those that have bound to the second solid phase containing silica.

2. The method for nucleic acid isolation according to claim 1, wherein nucleic acids that bind to the first solid phase containing silica are composed of not less than 20000 deoxyribonucleotides or ribonucleotides and nucleic acids that bind to the second solid phase containing silica are composed of not more than 10000 deoxyribonucleotides or ribonucleotides.

3. The method for nucleic acid isolation according to claim 1, wherein nucleic acids that bind to the first solid phase containing silica are composed of not less than 50000 deoxyribonucleotides or ribonucleotides.

4. The method for nucleic acid isolation according to claim 1, wherein nucleic acids that bind to the second solid phase containing silica are composed of not more than 5000 deoxyribonucleotides or ribonucleotides.

5. The method for nucleic acid isolation according to claim 1, wherein nucleic acids that bind to the first solid phase containing silica are genomic DNA and nucleic acids that bind to the second solid phase containing silica are RNA.

6. The method for nucleic acid isolation according to claim 1, wherein nucleic acids that bind to the first solid phase containing silica are genomic DNA and nucleic acids that bind to the second solid phase containing silica are plasmid DNA.

7. A kit for nucleic acid isolation comprising:
   a chaotropic agent to be mixed with a sample solution containing nucleic acids,
   at least two kinds of instruments for nucleic acid isolation, each instrument being equipped with a solid phase containing silica with a certain pore size different from others and with a passage opening at one end and a connection opening at another end configured to attach to a syringe controlling liquid by pressure through the passage opening,
   a washing reagent for washing the solid phases, and
   an elution reagent for eluting the nucleic acids from the solid phases:
   wherein said pore sizes of two instruments of the at least two kinds of instruments are of 20-25 µm and 0.1-10 µm.

8. The kit for nucleic acid isolation according to claim 7, further comprising: at least a kind of organic solvent to he added to mixture of the chaotropic agent and the sample.

9. The kit for nucleic acid isolation according to claim 8, wherein the organic solvent is ethanol and/or diethylene glycol dimethyl ether.

* * * * *